United States Patent [19]
Allemand

[11] 4,055,767
[45] Oct. 25, 1977

[54] DETECTION APPARATUS FOR X-RAY TOMOGRAPHY

[75] Inventor: Robert Allemand, Saint Ismier, France

[73] Assignee: Commissariat a l'Energie Atomique, Paris, France

[21] Appl. No.: 692,735

[22] Filed: June 4, 1976

[30] Foreign Application Priority Data

June 19, 1975 France ............................... 75.19263

[51] Int. Cl.² .............................................. G01T 1/18
[52] U.S. Cl. .................................. 250/385; 250/445 T
[58] Field of Search .................. 250/445 T, 385, 363 S

[56] References Cited

U.S. PATENT DOCUMENTS

| 3,703,638 | 11/1972 | Allemand et al. ................... 250/385 |
| 3,881,110 | 4/1975 | Hounsfield et al. ............. 250/445 T |
| 3,991,312 | 11/1976 | Whetten et al. ...................... 250/385 |

*Primary Examiner*—Davis L. Willis
*Attorney, Agent, or Firm*—Lane, Aitken, Dunner & Ziems

[57] ABSTRACT

In a device comprising one or a number of X-ray beams of suitable shape and at least one cell for detecting X-rays which have passed through the organ to be analyzed, the detection cells are ionization chambers comprising two parallel electrodes separated by a radiation-detecting medium for converting the X-rays to electron-ion pairs. The electrodes are connected to two terminals of a voltage source and the detection cells are associated with means for measuring the charge collected during a predetermined period of time under the influence of the X-rays.

9 Claims, 4 Drawing Figures

DETECTION APPARATUS FOR X-RAY TOMOGRAPHY

This invention relates to an analytical device for transmission X-ray tomography.

It is known that a certain number of instruments are commercially available for measuring the density of tissue of an organ in a given plane of section.

The principle of these instruments is based on the measurement of the absorption of an X-ray beam, the absorption being a function of the density of the tissues examined.

If it is desired to draw up a density map of an organ, it is possible in accordance with a known technique to transmit a very narrow X-ray beam in a plane of this tissue and to observe the absorption corresponding to each position of the X-ray beam. A plurality of sweeps in crossed directions makes it possible, after suitable numerical processing of the series of absorption measurements preferentially carried out in a computer, to determine the value of X-ray absorption at one point of the plane of section considered and thus to determine the density of the tissues.

In the instrument which is marketed by the British company known as E.M.I. (Electrical and Musical Industries Limited), about one hundred absorption measurements are carried out during a single sweep which lasts approximately 1 second; the number of sweeps performed in this apparatus is 180 and the rotation of the X-ray emitter and of the associated receiver about the body to be studied takes place in the section plane of said body, degree by degree over a semicircle around the organ.

A total of 18,000 measurements can be obtained by means of this instrument which serves to draw up a map of the brain in the form of a matrix of 80 × 80, each point of the matrix being a cell of side 3 mm. Accuracy in the measurement of density is of the order of 0.5%, which makes it possible to draw the map of the brain to a density scale of approximately 10 levels. The examination time, however, is of the order of 3 minutes.

In order to extend this examination to organs other than the brain, it is necessary to employ much shorter examination times. In fact, although it is a relatively easy matter to maintain a head or cranium motionless for a period of 3 minutes, it is not possible to contemplate examinations of this length in the case of other organs since respiratory and abdominal movements, for example, have a blurring effect which impairs the quality of the images to an appreciable extent.

It is therefore necessary to reduce the examination times to a few seconds approximately.

In devices of this type which are commercially available, the beam of X-rays is emitted in the form of a narrow pencil and received by a single and movable X-ray detector; designs have also been proposed in which the X-ray beam is flat and divergent and in which it is received by a plurality of stationary X-ray detectors; the detectors employed in the prior art are scintillation detectors formed by a NaI scintillator, for example, which is subjected to the X-ray beam and followed by a photomultiplier.

One of the aims of the present invention is to provide an analytical device for X-ray tomography which permits an appreciable reduction of the observation time required for measuring the density in one section of an organ.

In accordance with the invention, the detection cell or cells employed are ionization chambers, that is, detection cells comprising two parallel electrodes which are separated by a radiation-detecting medium for converting the X-rays to electron-ion pairs and which are connected to two terminals of a voltage source, said detection cells being associated with means for measuring the charge collected in each cell during a predetermined period of time under the influence of the X-rays which have passed through the organ under examination.

Preferentially, the analytical device for transmission X-ray tomography in accordance with the invention comprises a wide source of X-rays for directing an X-ray beam having a wide range of angular divergence (between 10° and 120°) but a small thickness (between 0.1 mm and 20 mm) onto an organ to be studied, and a multicellular ionization chamber composed of a plurality of detection cells.

As a general rule, the cell is a gas-filled ionization chamber and the device further comprises means whereby the assembly consisting of X-ray source and ionization chamber is caused to rotate simultaneously about a common point located substantially at the center of said organ in order to carry out a plurality of crossed sweeps with a view to determining the absorption of an organ to be studied at each point of the section plane.

Further properties and advantages of the invention will become apparent from the following description of exemplified embodiments which are given by way of explanation and not in any limiting sense, reference being made to the accompanying drawings, wherein.

Figure 1:
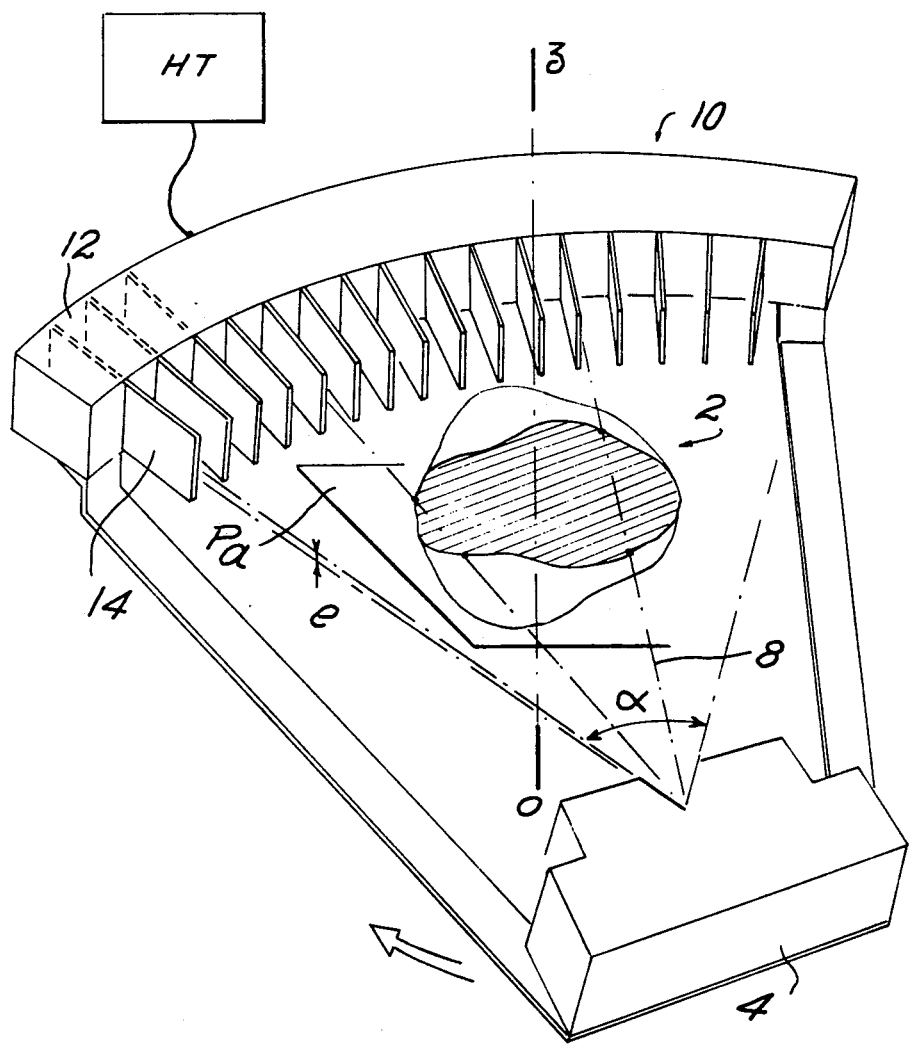
FIG. 1 is a perspective view of an X-ray analytical device in accordance with the invention.

The analytical device in accordance with the invention as shown in FIG. 1 is intended to analyze the organ 2 along the plane of section Pa. The device comprises an X-ray generator 4 which delivers an X-ray beam 8 having a divergence angle $\alpha$ at the vertex and a very small thickness $e$ onto the organ 2 to be studied. A multiple ionization chamber 10 formed by a plurality of detection cells 12 receives the X-ray beam, part of which has passed through the organ 2. Said chamber measures the intensity of the X-ray beam which penetrates into each of the cells 12 after collimation through the slits such as 14 which eliminate scattered radiation from the organ. The assembly consisting of X-ray generator and multiple ionization chamber is capable of rotating about an axis of rotation Oz which passes substantially through the center C of the plane of section Pa of the organ 2, the axis Oz being perpendicular to said plane.

The device proposed comprises a multiple ionization chamber 10 which operates at a high pressure in order to obtain good detection efficiency within the energy range of the X-ray beams employed and emitted by the generator 4 (100 to 160 KeV).

The device described makes it possible to suppress the translational motion of the monodetector generator assembly by making use of a multidetector. The X-ray generator is collimated so as to irradiate the entire organ in the plane of section P*a* considered.

The degree of accuracy achieved in the measurement of density is a function of the statistical accuracy of each measurement. In order to improve the statistical accuracy, a large number of events has to be counted. It is necessary to ensure that the number of events to be detected is at least equal to $5 \times 10^4$ events approximately in the case of each measurement (degree of accuracy equal to the reciprocal of the square root of the number of events, namely of the order of 0.5%). Postulating a total examination time of 5 seconds and considering 200 measurements at the time of rotation of the generator and ionization chamber assembly through an angle of 180°, it is apparent that the minimum count rate is $5 \times 10^4$ events at intervals of 25 milliseconds or $2 \times 10^6$ events per second. Specifying that the intensity of the least absorbed beam (at the periphery of the organ) is approximately one hundred times higher, the maximum count rate must consequently be of the order of $2 \times 10^8$ events per second. No detection device is capable of achieving a rate of this order and it has consequently been found necessary to measure the mean current delivered by the cells.

The cells of the ionization chamber can be solid ionization cells such as the cadmium telluride or mercury iodide cells or, preferentially, a gas-filled ionization chamber consisting of multiple detection cells. Detection cells of the gas-filled type in current use have the outstanding advantage of a short charge transit time.

The use of an ionization chamber comprising a plurality of identical detection cells represents a considerable improvement over devices consisting of several hundred individual and independent scintillation detectors and a corresponding number of photomultipliers. In fact, while it proves necessary to ensure that measurements are taken with a degree of accuracy of the order of a few thousandths (of the same order of magnitude as the statistical accuracy of measurements), it does not seem to be possible for reasons of reproducibility of organs to attain this level of accuracy by means of an assembly formed by at least 100 photomultipliers, for example. By adopting a detector of the ionization chamber type, it is possible on the one hand to obtain better stability in the measurements of current by virtue of the design principle of this detector and on the other hand to obtain better uniformity of response by making use of a single multi-cell chamber.

The measurement of the intensity of the X-ray beam which had passed through the organ to be studied is carried out by means of a multiple ionization chamber 10 comprising a certain number of juxtaposed cells 12 filled with an inert gas having a high stopping power (xenon, for example) at a fairly high pressure (10 to 20 bar) in order to achieve a high degree of detection efficiency.

The detector assembly is in the form of a circular arc centered on the X-ray generator. The radius of curvature is selected so as to permit sectional mapping of the entire organ and is of the order of 120 cm.

The dimensions and number of the cells are determined from the definition of the image which it is sought to obtain. In the case of an array of 160 detection cells having a pitch of 7 mm approximately, the angle of the angular sector $\alpha$ is in the vicinity of 50°. The depth of detection is determined so as to obtain good collection of the X-rays; at a pressure of 12 bar of xenon, a thickness of 10 cm ensures a detection efficiency which is higher than 70%.

Figure 2:
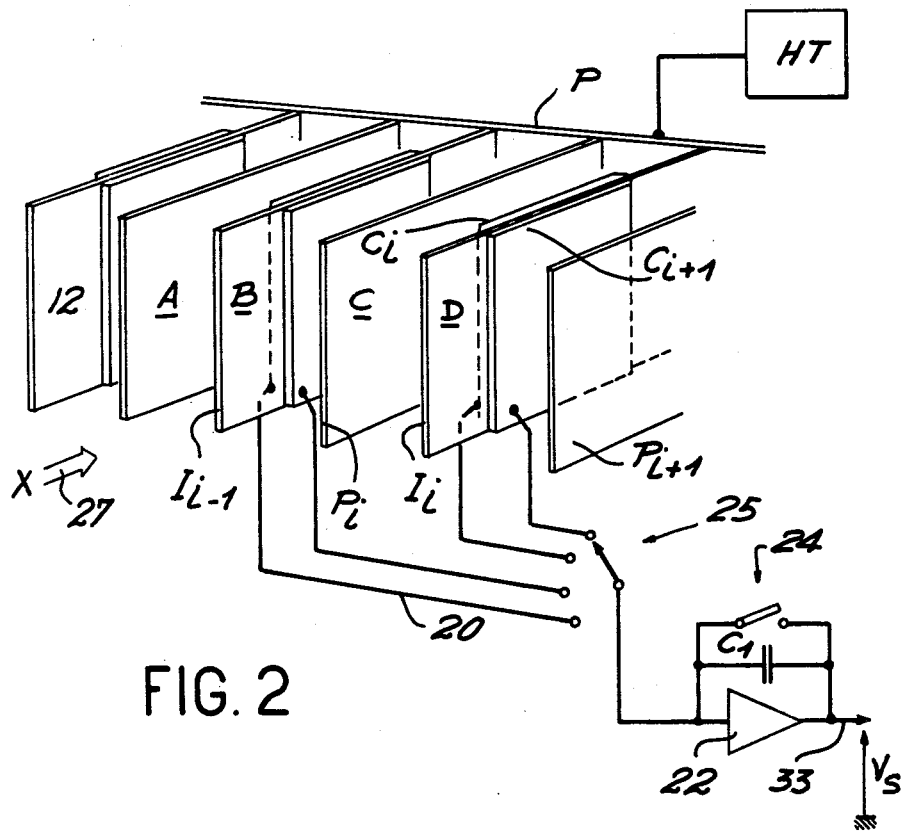
FIG. 2 is a diagram of one embodiment of the multiple ionization chamber in accordance with the invention.

One embodiment of the multiple ionization chamber comprising a number of detection cells is shown in FIG. 2. In this embodiment, the anode is constituted by a plate P on which are fixed a plurality of perpendicular plates $P_i$, the plates P and $P_i$ being brought to a positive high voltage. The cathodes are constituted by plates $C_i$ located opposite to the anode plates $P_i$. The space between each anode and each cathode constitutes a gas-filled detection cell such as the cell 12 in which the X-rays form electron-ion pairs, that is, charges which move towards the anode and the cathode. The leads such as those designated by the reference 20 are connected to a device for measuring the charge developed per unit of time in one cathode. The cathode plates $C_i$ and $C_{i+1}$ are separated by an insulating plate $I_i$. In this example, there are shown four detection cells A, B, C and D, the four corresponding cathodes being connected to a measuring instrument constituted by an integrating amplifier 22. Each detection cell such as the cell 12 comprises the space located between an anode and a cathode and constitutes an ionization chamber. The geometrical arrangement of the cells is such that the anode and cathode electrodes serve as shields between the cells.

The photoelectric effect in xenon of an X-ray having an energy E produces an electron of energy $E - E_k$, where $E_k$ is the binding energy of an electron of the xenon layer K, that is approximately 30 keV; there then takes place an electron rearrangement by emission of X-radiation of 30 keV energy. Whereas the photoelectric electron is clearly detected in the cell considered, the X-radiation of 30 keV energy is liable to be detected within the adjacent cells and thus to provide false information. It is in order to prevent this phenomenon that the electrodes also have a shielding function between the cells in order to ensure better collimation of the input beam and also to prevent the parasitic X-radiation from passing from one cell to the next. It is readily apparent that the array of cells is placed within a leak-tight enclosure in which the pressure of xenon is of the order of approximately ten atmospheres.

Another important feature of a chamber of this type is the charge collection time. In order to prevent errors of measurement, it is in fact necessary to ensure that the collection time is considerably shorter than the scanning frequency which is of the order of 25 milliseconds. An experimental check has shown that, in the case of an interelectrode space of 7 mm and an operating voltage of 5 kV between the anode and the cathode, the collection time is shorter than 2 milliseconds. The charges collected on the cathode during periods of this length are of the order of a few $10^{-10}$ Coulomb. This charge which is stored in the plates will be read at 25-millisecond intervals by a low-level field-effect transistor scanner as shown in FIG. 2. The output signal $V_S$ obtained on channel 33 by integration of the charge Q developed on a cathode is given by the formula:

$$V_S = (Q/C_1)$$

From one cell to the next, the capacitor $C_1$ is discharged by closing the short-circuit switch 24. The connection of each cell is established by means of the switching device 25. The electronic measuring system as well as the detail of reconstruction of density of tissues from multiple sweeps will not be described further since they are well known to those versed in the art. It is readily apparent that a construction in which provision is made for a number of measuring channels corresponding to the number of cells also forms part of the invention. The X-rays arrive at the chamber in the direction of the arrow 27.

Figure 3:
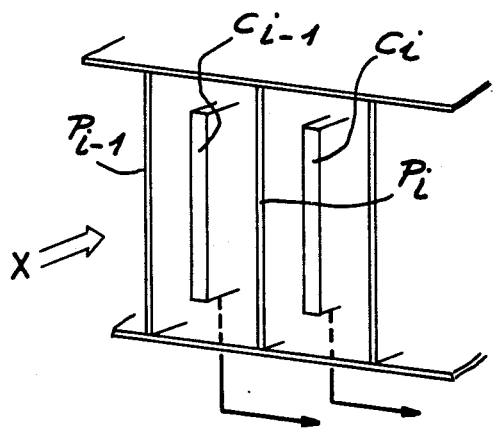
FIG. 3 shows an alternative embodiment of the multiple ionization chamber.

In FIG. 3, there is shown an alternative embodiment of the ionization chamber according to the invention in which, in order to prevent stray capacitances between cathodes in the configuration shown in FIG. 2, each cathode has been spaced so as to insert this latter in the form of a plate between two anodes $P_{i-1}$ and $P_i$. In this configuration, the cathode is located at the center of each cell. The charges collected by the cathodes $C_i$ are measured as in the example shown in FIG. 2.

Figure 4:
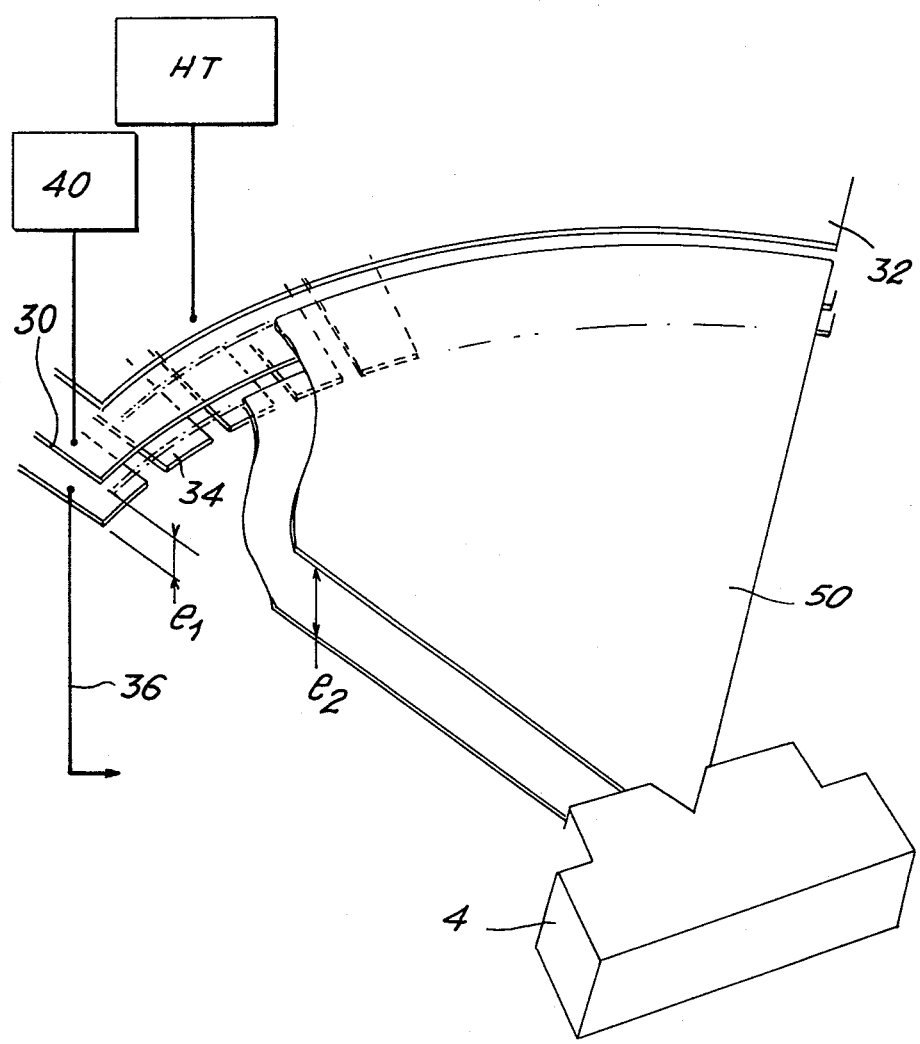
FIG. 4 shows an alternative embodiment of the multiple ionization chamber comprising an accelerating grid.

In FIG. 4, there is shown the detail of an ionization chamber in accordance with the invention comprising a screen grid 30. In this embodiment, a single cathode 32 is connected to a negative high-voltage source. A plurality of anodes such as those designated by the reference 34 are connected by means of leads such as the lead 36 to an amplifying and scanning device which is similar to that shown in FIG. 2.

The grid 30 is located directly above these multiple anodes; the distance between two anodes defines the dimensions of a cell. Within the space formed between anode and grid and having a thickness $e_1$, the electrons are collected by the anodes such as the anode 34. The useful zone having a thickness $e_2$ of the charge-generating X-ray beam is located between the grid 30 and the cathode 32. Screens which are opaque to X-rays such as the screen 50 extend opposite to the cathode 32 and the grid 30 from the X-ray source so as to delimit this useful zone. The device of FIG. 4 permits of more rapid studies, especially for images of moving organs, the measurement time being reduced. The grid delimits with the cathode 32 the detection zone proper of thickness $e_2$, that is, the zone in which the X-radiation interacts with the ionizable gas (xenon, for example). The grid 30 which is brought to the potential $-V_1$ (lower at absolute value than the potential $V_2$ of the plate 32) by means of a supply 40 performs the functon of electrostatic screen for the anode in regard to the signals induced by the ions which are directed towards the cathode and has a sufficient degree of transparency (80%) to the electrons which are directed towards the anodes. The anode signals collected are therefore produced solely by the electrons. Since the electron mobilities will be approximately one thousand times greater than the ion mobilities, the charge collection times will be reduced accordingly.

In the case of the diagram shown in FIG. 4, it is apparent that no provision is made for shields between the cells in the embodiment which is illustrated in order to avoid the disadvantage arising from X-fluorescence radiation in the xenon but it is possible to incorporate insulating plates in the height of the useful zone in order to overcome this disadvantage.

Although the invention has been described with reference to embodiments comprising a multicellular ionization chamber, it should be pointed out that the invention also extends to the devices which comprise a plurality of independent ionization chambers associated with an X-ray source which delivers a flat and divergent beam as well as to devices comprising a single ionization chamber associated with an X-ray source which delivers a narrow pencil. Thus the primary advantage of the invention in fact lies in the use of a detector of the ionization chamber type and of a means for measuring the mean current delivered by said detector. This arrangement makes it possible to reduce the observation time which is necessary for tomographic analysis.

What we claim is:

1. Detection apparatus for use with X-ray tomography apparatus comprising at least one X-ray source adapted to emit X-ray beams to pass through an organ to be analyzed and to thereupon be intercepted by said detection apparatus which comprises multicellular ionization chambers constituted by a single comb-type anode formed by a substantially cylindrical first plate p and a plurality of flat plates $P_i$ at right angles to said plate P and a plurality of cathodes $C_i$, each being formed by a plate which is parallel to one of said plates $P_i$, each of said chambers comprising two substantially parallel anode and cathode electrodes separated by a radiation-detecting medium adapted to convert the incident X-rays to electron-ion pairs, a voltage source connected to said electrodes, and means connected to said electrodes for measuring the charge collected during a predetermined time interval under the influence of the incident X-rays.

2. Detection apparatus for use with X-ray tomography apparatus according to claim 1 wherein said X-ray source includes means for directing an X-ray beam having a range of angular divergence between 10° and 120° and a small thickness in a range between 0.1 mm and 20 mm onto an organ to be analyzed.

3. Detection apparatus for use with X-ray tomography apparatus according to claim 1 comprising means for simultaneously rotating said X-ray source and said multicellular ionization chambers about a point located substantially at the center of an organ to be analyzed.

4. Detection apparatus for use with X-ray tomography apparatus according to claim 1 wherein two successive cathodes $C_i$ and $C_{i+1}$ are applied against an insulating plate $I_i$ which is parallel to the plates $P_i$ for each index value "i".

5. Detection apparatus for use with X-ray tomography apparatus according to claim 1 wherein each cathode plate is placed at an equal distance between two successive anode plates.

6. Detection apparatus for use with X-ray tomography apparatus according to claim 1 wherein said charge-measuring means comprises an integrating amplifier.

7. Detection apparatus for use with X-ray tomography apparatus according to claim 6 further comprising switching means for connecting successively N cathodes forming part of N chambers to said integrating amplifier.

8. Detection apparatus for use with X-ray tomography apparatus according to claim 1 wherein each ionization chamber is filled with xenon gas at a pressure of approximately ten atmospheres.

9. Detection apparatus for use with X-ray tomography apparatus comprising at least one X-ray source adapted to emit X-ray beams to pass through an organ to be analyzed and to thereupon be intercepted by said detection apparatus which comprises multicellular ionization chambers constituted by a series of anode plates positioned parallel to each other and parallel to the direction of propagation of the X-rays, a grid positioned parallel to said anode plate and being brought to a negative potential $-|V_1|$, and a cathode plate positioned parallel to said anode plates and so that said grid is between said cathode plate and said anode plates, said cathode plate being brought to a negative potential $|V_2| > |V_1|$, a radiation detecting medium adapted to convert the incident X-rays to electron-ion pairs, and means connected to said anode plates for measuring the charges collected during a predetermined time interval under the influence of the incident X-rays.

* * * * *